United States Patent
Lee et al.

(10) Patent No.: US 10,682,264 B2
(45) Date of Patent: Jun. 16, 2020

(54) DIAPER PANTS HAVING A PARTIAL NON-OVERLAPPING WAIST PANEL STRUCTURE FREE OF INNER MATERIAL AND ELASTICS

(71) Applicant: Kimberly-Clark Worldwide, Inc., Neenah, WI (US)

(72) Inventors: Sang Hyun Lee, Yongin-Si (KR); DongSoo Choi, Yongin-Si (KR); KyungSik Jang, Yongin-Si (KR); Minyoung Jeon, Yongin-Si (KR); Allyssa Marie Herrmann, Yongin-Si (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 15/566,138

(22) PCT Filed: Dec. 16, 2016

(86) PCT No.: PCT/US2016/067129
§ 371 (c)(1),
(2) Date: Oct. 12, 2017

(87) PCT Pub. No.: WO2018/111298
PCT Pub. Date: Jun. 21, 2018

(65) Prior Publication Data
US 2018/0353350 A1    Dec. 13, 2018

(51) Int. Cl.
*A61F 13/493* (2006.01)
*A61F 13/49* (2006.01)
*A61F 13/496* (2006.01)

(52) U.S. Cl.
CPC .... *A61F 13/49011* (2013.01); *A61F 13/4902* (2013.01); *A61F 13/496* (2013.01); *A61F 2013/49025* (2013.01)

(58) Field of Classification Search
CPC ............ A61F 13/49058; A61F 13/4906; A61F 13/49061; A61F 2013/49025; A61F 2013/49033
(Continued)

(56) References Cited

U.S. PATENT DOCUMENTS 4,596,568 A    6/1986  Flug
4,887,602 A   12/1989  Oleary
(Continued)

FOREIGN PATENT DOCUMENTS

CN    201267569 Y    7/2009
CN    203576760 U    5/2014
(Continued)

*Primary Examiner* — Susan S Su
(74) *Attorney, Agent, or Firm* — Kimberly-Clark Worldwide, Inc.

(57) ABSTRACT

An absorbent article includes a longitudinal axis and a lateral axis; a front region, a back region, a crotch region, the crotch region being disposed between the front region and the back region; a front panel in the front region, wherein the front panel includes an inner layer and an outer layer; a back panel in the back region, wherein the back panel includes an inner layer and an outer layer; an elastic layer disposed between the inner layer and the outer layer in the front panel; an elastic layer disposed between the inner layer and the outer layer in the back panel; and a single-layer zone in one of the front and back panels, wherein the single-layer zone is free of the inner layer and elastic layer.

20 Claims, 5 Drawing Sheets

(58) Field of Classification Search
USPC .................................................. 604/358–392
See application file for complete search history.

(56) References Cited

U.S. PATENT DOCUMENTS

| | | | |
|---|---|---|---|
| 5,137,525 A | 8/1992 | Glassman | |
| 5,451,217 A | 9/1995 | Fujioka et al. | |
| 5,571,096 A | 11/1996 | Dobrin et al. | |
| 5,685,874 A | 11/1997 | Buell et al. | |
| 5,843,057 A | 12/1998 | McCormack | |
| 5,879,341 A | 3/1999 | Odorzynski et al. | |
| 6,152,906 A | 11/2000 | Faulks et al. | |
| H1969 H | 6/2001 | Fell et al. | |
| 6,277,479 B1 | 8/2001 | Campbell et al. | |
| 6,413,247 B1 | 7/2002 | Carlucci et al. | |
| 6,450,997 B1 | 9/2002 | Seitz et al. | |
| 6,679,869 B1 | 1/2004 | Schlinz et al. | |
| 7,435,244 B2 | 10/2008 | Schroer, Jr. et al. | |
| 8,101,814 B2 | 1/2012 | Mirle et al. | |
| 9,168,182 B2 | 10/2015 | Hargett et al. | |
| 2001/0039405 A1 | 11/2001 | Keuhn et al. | |
| 2003/0135185 A1 | 7/2003 | Crowther | |
| 2004/0147890 A1 | 7/2004 | Nakahata et al. | |
| 2005/0043699 A1 | 2/2005 | Minato | |
| 2005/0203475 A1 | 9/2005 | Lavon et al. | |
| 2005/0261647 A1 | 11/2005 | Karami et al. | |
| 2008/0132867 A1 | 6/2008 | Damaghi et al. | |
| 2010/0145295 A1 | 6/2010 | Isele et al. | |
| 2011/0077609 A1* | 3/2011 | Kuwano | A61F 13/49011 |
| | | | 604/385.01 |
| 2011/0098668 A1* | 4/2011 | Thorson | A61F 13/49012 |
| | | | 604/385.25 |
| 2011/0319853 A1 | 12/2011 | Yamashita et al. | |
| 2012/0310193 A1 | 12/2012 | Ostertag | |
| 2013/0281955 A1 | 10/2013 | Kobayashi et al. | |
| 2013/0317468 A1* | 11/2013 | Yoshioka | A61F 13/15593 |
| | | | 604/361 |
| 2015/0032072 A1* | 1/2015 | Hashimoto | A61F 13/496 |
| | | | 604/385.21 |
| 2015/0051569 A1* | 2/2015 | Hashimoto | A61F 13/496 |
| | | | 604/385.16 |
| 2015/0148768 A1* | 5/2015 | Fukasawa | A61F 13/49011 |
| | | | 604/385.16 |
| 2017/0112683 A1* | 4/2017 | Fukasawa | A61F 13/49011 |

FOREIGN PATENT DOCUMENTS

| | | |
|---|---|---|
| CN | 203841922 U | 9/2014 |
| CN | 204169995 U | 2/2015 |
| CN | 204274808 U | 4/2015 |
| EP | 0 422 504 A2 | 4/1991 |
| GB | 2 268 389 B | 7/1996 |
| JP | 2013-034850 A | 2/2013 |
| KR | 10-2012-0003790 A | 1/2012 |
| ZA | 1995/09258 A | 5/1996 |

* cited by examiner

DIAPER PANTS HAVING A PARTIAL NON-OVERLAPPING WAIST PANEL STRUCTURE FREE OF INNER MATERIAL AND ELASTICS

BACKGROUND

Absorbent articles, such as diapers, incontinence garments, training pants, sanitary napkins, panty liners, and the like are well known in the art. These articles, which are often disposable, are capable of absorbing and retaining fluids and other bodily discharges. Some absorbent articles, such as pull-on type absorbent articles, include a central absorbent member and side panels extending from and interconnecting respective front and back regions of the absorbent member forming a waist assembly.

Some known absorbent articles include liquid impermeable side panels to prevent liquid discharged by a wearer from leaking through the side panels. Such side panels can be impervious to water vapor as well as liquid. Side panels that are impermeable to both liquids and water vapor can cause the absorbent article often to feel hot and clammy to the wearer, especially after a bodily discharge. Furthermore, the lack of permeability to both liquid and water vapor can cause irritation to the skin of the wearer around the waist. In addition to concerns over skin wellness, liquid impermeable side panels often lack aesthetic and tactile qualities desired in absorbent articles.

From a product standpoint, an absorbent article in the diaper pants format can give an impression of being too stuffy and bulky to a caregiver because the diaper pant is in an enclosed form with the exception of the waist and leg openings. In addition, there can be 20 to 30 high-tension elastics embracing the waist area, which add to the perception of stuffiness. These issues with the use of diaper pants are especially unfavorable to babies living in hot and humid countries where excessive sweating can lead to many health and skin issues.

Diaper pants, due to their relatively short history, have not changed much with respect to visual differences around the waist panel. Prior art examples offer a very similar look and function around the waist, notably a typical double-layer system with waist elastics being sandwiched between outer material and inner material using adhesive.

In addition, efforts to deliver better breathability around the waist area have merely focused on changing the material type of waist panel. For example, using apertured material (i.e., those that have tiny holes) has been explored consistently, but the level of improvement is still limited by the double-layer system.

SUMMARY

Significant improvements in appearance and breathability can be achieved using a structural approach in addition to the material approach described above. Taking a structural approach delivers an additional degree of flexibility when trying to improve breathability. The technology described herein introduces a partial zone that bypasses the conventional methods by offering an inner material-free zone with no elastics or adhesives.

In an aspect, an absorbent article includes a longitudinal axis and a lateral axis; a front region, a back region, a crotch region, the crotch region being disposed between the front region and the back region; a front panel in the front region, wherein the front panel includes an inner layer and an outer layer; a back panel in the back region, wherein the back panel includes an inner layer and an outer layer; an elastic layer disposed between the inner layer and the outer layer in the front panel; an elastic layer disposed between the inner layer and the outer layer in the back panel; and a single-layer zone in one of the front and back panels, wherein the single-layer zone is free of the inner layer and elastic layer.

In another aspect, an absorbent article includes a longitudinal axis and a lateral axis; a front region, a back region, a crotch region, the crotch region being disposed between the front region and the back region; a front panel in the front region, wherein the front panel includes an inner layer, an outer layer, and an elastic layer; a back panel in the back region, wherein the back panel includes an inner layer, an outer layer, and an elastic layer; and a single-layer zone in each of the front and back panels, wherein each single-layer zone is free of the inner layer and elastic strands.

In still another aspect, an absorbent article includes a longitudinal axis and a lateral axis; a front region, a back region, a crotch region, the crotch region being disposed between the front region and the back region; a central absorbent assembly; a front panel in the front region, wherein the front panel includes an inner layer, an outer layer, and a plurality of elastic strands; a back panel in the back region, wherein the back panel includes an inner layer, an outer layer, and a plurality of elastic strands; and a single-layer zone in each of the front and back panels, wherein each single-layer zone is free of the inner layer and elastic strands, and wherein each single-layer zone divides the elastic layer of the panel into two longitudinally-separate elastic layer regions.

DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
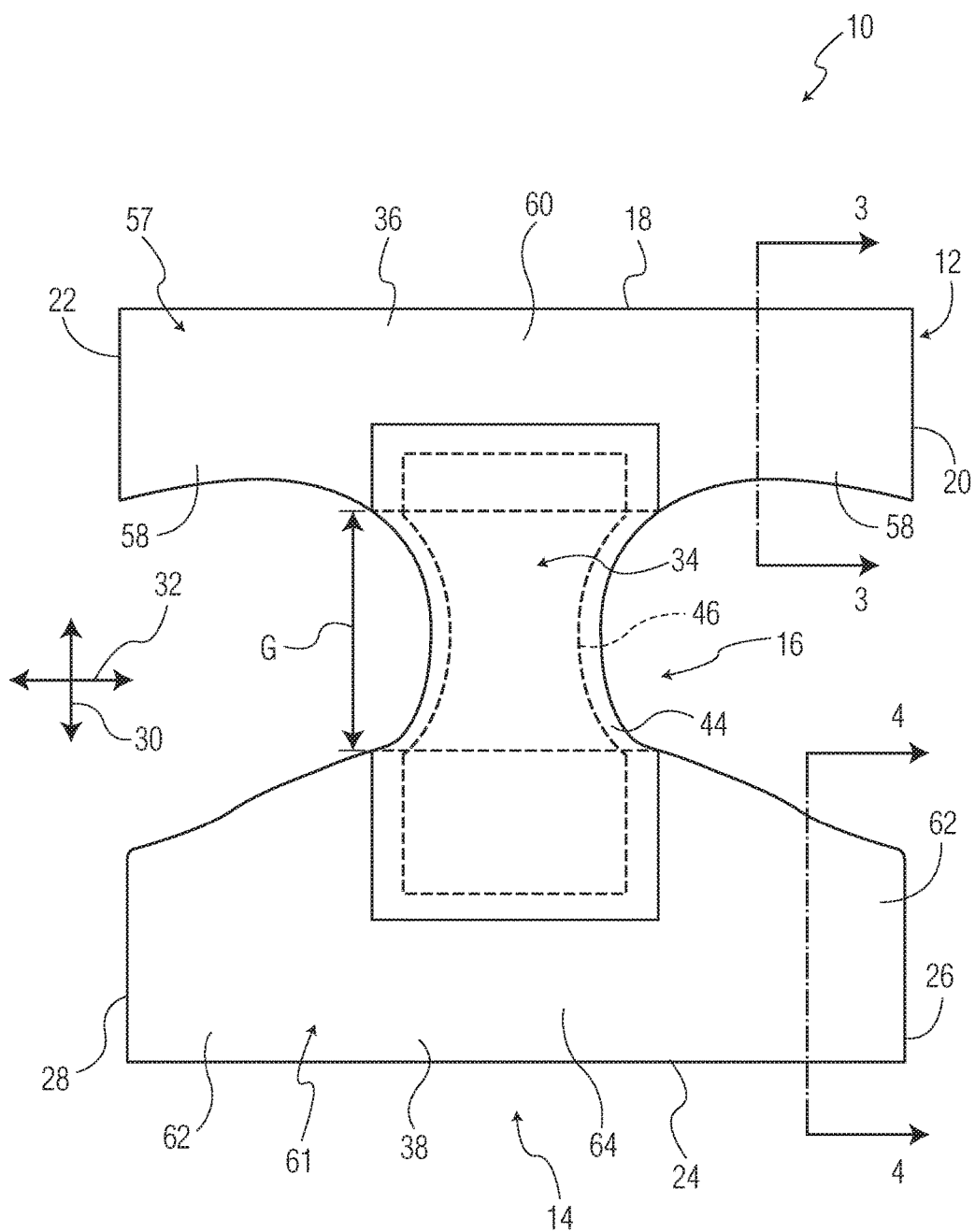
FIG. 1 is a top down view of an aspect of an absorbent article of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

The term "absorbent article" refers herein to an article that can be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple fibers typically having fiber lengths less than about 100 mm. Bales of staple fibers can undergo an opening process to separate the fibers that are then sent to a carding process that separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers can be subject to adhesive processes to bind the fibers together such as by the use of powder adhesives. The carded web can be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films that constitute liquid transfer films, as well as films that do not transfer fluids, such as, but not limited to, barrier films, filled films, breathable films, and oriented films.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers that can be continuous or discontinuous, are generally smaller than about 0.6 denier, and can be tacky and self-bonding when deposited onto a collecting surface.

The term "nonwoven" refers herein to materials and webs of material that are formed without the aid of a textile weaving or knitting process. The materials and webs of materials can have a structure of individual fibers, filaments, or threads (collectively referred to as "fibers") that can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials that are compliant and that will readily conform to the general shape and contours of the wearer's body.

The term "spunbond" refers herein to small diameter fibers that are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an aspect, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an aspect, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a polymeric material that becomes pliable or moldable above a specific temperature and returns to a solid state upon cooling.

Generally, an absorbent article is disclosed herein.

Figure 2:
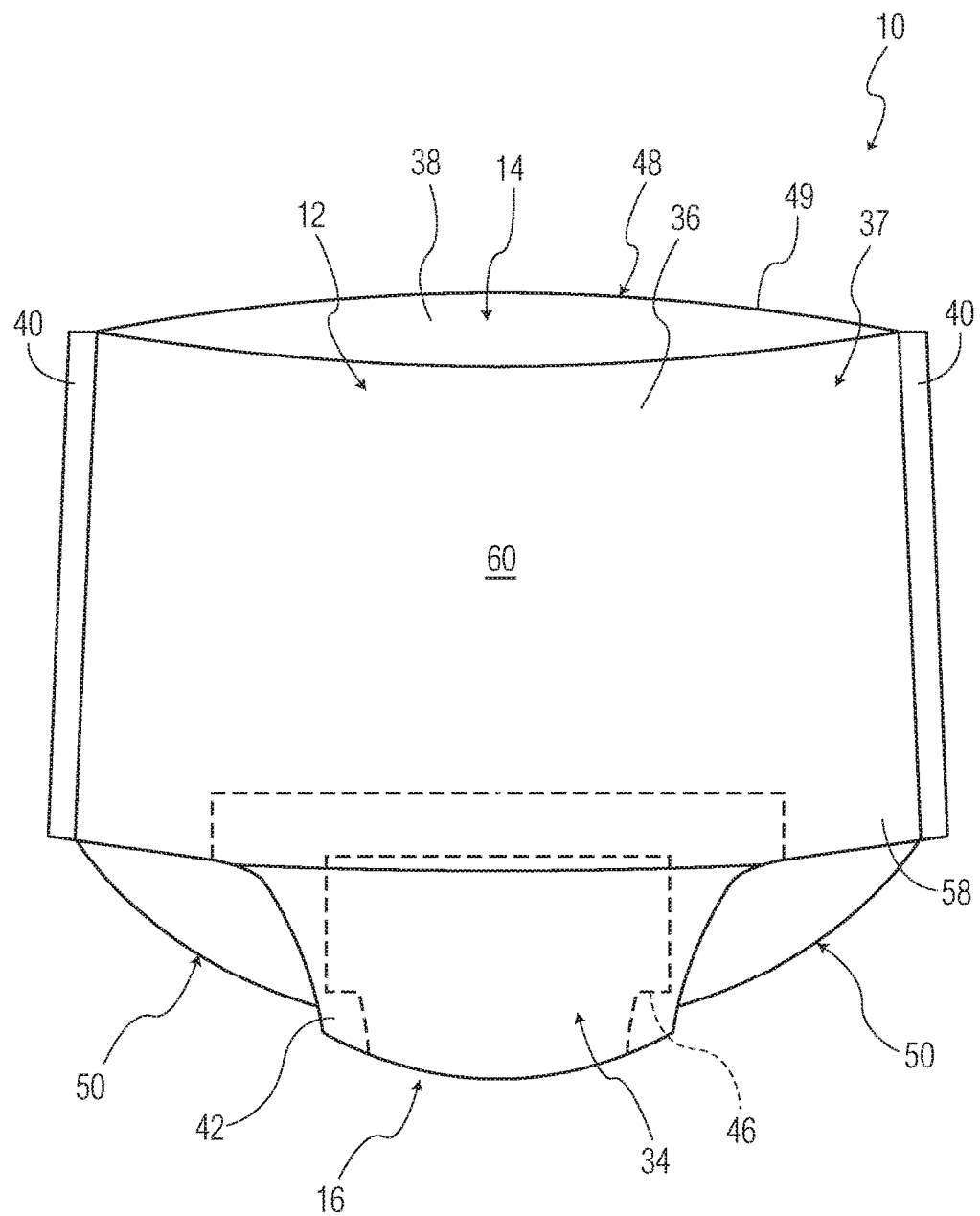
FIG. 2 is an elevation view of the front of the absorbent article of FIG. 1, in an assembled condition.

With reference to the drawings, FIGS. 1 and 2 illustrate one suitable aspect of an absorbent article of the present disclosure in the form of a diaper pant, indicated generally at 10. While the present disclosure will be made in the context of the diaper pant 10, it should be understood that aspects of the present disclosure are applicable to other absorbent articles, such as, for example, refastenable diapers, adult incontinence garments, children's training pants, swim diapers, feminine care articles, and the like.

In one suitable aspect, the diaper pant 10 is a disposable absorbent article. As used herein, the term "disposable absorbent article" refers to articles that absorb and contain body exudates and that are intended to be discarded after a limited period of use. The articles are not intended to be laundered or otherwise restored for reuse. The articles can be placed against or in proximity to the body of a wearer to absorb and contain various exudates discharged from the body. It is understood that in other suitable aspects, the diaper pant 10 (or more broadly, the absorbent article) can be reusable. That is, the absorbent article can be intended for multiple uses without departing from some aspects of this disclosure.

FIG. 1 illustrates the diaper pant 10 in an unfolded and laid flat condition to show an inner surface of the diaper that faces the wearer when the diaper is worn.

With reference still to FIG. 1, the diaper pant 10 has a longitudinal direction 30 and a lateral direction 32. In the longitudinal direction 30, the diaper pant 10 defines a front region 12, a back region 14, and a crotch region 16 extending between and connecting the front region 12 and the back region 14.

In the front region 12, the diaper pant 10 has a front edge 18 and transversely opposed first and second front side edges 20, 22. A back edge 24 and transversely opposed first and second back side edges 26, 28 are located in the back region 14 of the diaper pant 10. In the illustrated aspect, the front edge 18 and the back edge 24 are straight edges. That is, the front edge 18 and the back edge 24 are substantially free from curves, bends, angles, notches or irregularities. It is understood, however, that the front edge 18 and/or the back edge 24 can be cut in any suitable shape as is known in the art (e.g., arcuate).

The diaper pant 10 includes a central absorbent assembly, indicated generally at 34, that extends longitudinally from the front region 12 through the crotch region 16 to the back region 14. The central absorbent assembly 34 of the illustrated aspect includes an outer cover 42 and a bodyside liner 44 connected to the outer cover 42 in a superposed relation by suitable means such as adhesives, ultrasonic bonds, thermal bonds, pressure bonds, or combinations thereof. An absorbent structure 46 is disposed between the outer cover 42 and the bodyside liner 44.

The front and back regions 12, 14 of the diaper pant 10 are constructed of separate pieces of elastic laminate 36, 38 that are interconnected via the absorbent assembly 34. That is, the front region 12 is formed by a piece of elastic laminate 36 and the back region 14 is formed by a separate piece of elastic laminate 38. In the illustrated aspect, each piece of laminate 36, 38 is attached to the outer cover 42 of the absorbent assembly 34 by suitable means such as adhesives, ultrasonic bonds, thermal bonds, pressure bonds, or combinations thereof. In other suitable aspects, the elastic laminates 36, 38 can be joined to other portions of the central absorbent assembly 34, such as the bodyside liner 44. As seen in FIG. 1, the laminate 36 forming the front region 12 is spaced from the laminate 38 forming the back region 14 to define a gap G. The absorbent assembly 34 spans the gap G and connects the laminate 36 forming the front region 12 to the laminate 38 forming the back region 14.

The laminate 36 used to form the front region 12 defines a front panel 57 including a pair of laterally opposite front side portions 58 extending outward from the absorbent assembly 34 at the front region 12, and a front central portion 60 disposed between the front side portions 58. The laminate 38 used to form the back region 14 defines a back panel 61 including a pair of laterally opposite back side portions 62 extending outward from the absorbent assembly 34 at the back region 14, and a back central portion 64 disposed between the back side portions 62.

As seen in FIG. 2, the laminate 36 used to form the front region 12 is joined to the laminate 38 used to form the back region 14 via a pair of non-refastenable butt (or fin) seams 40 to define a pull-on, pant-like configuration of the diaper pant 10 having a waist opening, indicated at 48, and two leg openings, indicated at 50. More specifically, each front side portion 58 is joined to a respective back side portion 62 via one of the non-refastenable butt seams 40.

With the diaper pant 10 in the pull-on, pant-like configuration, illustrated in FIG. 2, the front region 12 includes the portion of the diaper pant 10 that, when worn, is positioned at least in part on the front of the wearer while the back region 14 includes the portion of the diaper pant 10 that is positioned at least in part on the back of the wearer. The crotch region 16 of the diaper pant 10 includes the portion of the diaper pant 10 that is positioned between the legs of the wearer and covers the lower torso of the wearer. The front and back side portions 58, 62 include the portions of the diaper pant 10 (and more particularly of the front and back regions 12, 14) that, when worn, are positioned on the hips of the wearer.

As seen in FIG. 2, the laminates 36, 38 cooperatively define an elastic laminate waist assembly, indicated at 37, that defines the waist opening 48 of the diaper pant 10, and is configured to fully encircle the waist of the wearer. The elastic laminate waist assembly 37 includes the front panel 57 and the back panel 61. As described in more detail herein, the waist assembly 37 is sufficiently water-vapor permeable to provide a healthy and comfortable product for the wearer, but is also sufficiently liquid impermeable to inhibit bodily fluids from leaking through the waist assembly 37.

The central absorbent assembly 34 is configured to contain and/or absorb exudates discharged from the wearer. The outer cover 42 suitably includes a material which is substantially liquid impermeable. The outer cover 42 can be a single layer of liquid impermeable material, but more suitably includes a multi-layered laminate structure in which at least one of the layers is liquid impermeable. For instance, the outer cover 42 can include a liquid permeable outer layer and a liquid impermeable inner layer that are suitably joined together by an adhesive, ultrasonic bonding, thermal bonding, pressure bonding, or combinations thereof. Suitable adhesives can be applied continuously or intermittently as beads, a spray, parallel swirls, or the like. The liquid permeable outer layer can be any suitable material, including materials that provide a generally cloth-like texture. The outer layer can also be made of those materials of which the liquid permeable bodyside liner 44 is made. While it is not a necessity for the outer layer to be liquid permeable, it is suitable that it provides a relatively cloth-like texture to the wearer.

The inner layer of the outer cover 42 can be both liquid and vapor impermeable, or it can be liquid impermeable and vapor permeable. The inner layer can be manufactured from a thin plastic film, although other flexible liquid impermeable materials can also be used. The inner layer, or the liquid impermeable outer cover 42 when a single layer, prevents waste material from wetting articles, such as bed sheets and clothing, as well as the wearer and caregiver.

If the outer cover 42 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 42. One suitable "breathable" material is composed of a microporous polymer film or a nonwoven fabric that has been coated or otherwise treated to impart a desired level of liquid impermeability.

It is also contemplated that the outer cover 42 can be stretchable, and more suitably elastic. In particular, the outer cover 42 is suitably stretchable and more suitably elastic in at least the transverse, or circumferential direction of the pant 10. In other aspects the outer cover 42 can be stretchable, and more suitably elastic, in both the transverse and the longitudinal direction.

The liquid permeable bodyside liner 44 is illustrated as overlying the outer cover 42 and absorbent structure 46, and can, but need not, have the same dimensions as the outer cover 42. The bodyside liner 44 is suitably compliant, soft feeling, and non-irritating to the wearer's skin. The bodyside liner 44 is also sufficiently liquid permeable to permit liquid body exudates to readily penetrate through its thickness to the absorbent structure 46. Further, the bodyside liner 44 can be less hydrophilic than the absorbent structure 46 to present a relatively dry surface to the wearer and permit liquid to readily penetrate through its thickness. The hydrophilic/hydrophobic properties can be varied across the length, width and/or depth of the bodyside liner 44 and absorbent structure 46 to achieve the desired wetness sensation or leakage performance.

The bodyside liner 44 can be manufactured from a wide selection of web materials, such as porous foams, reticulated foams, apertured plastic films, woven and nonwoven webs, or a combination of any such materials. For example, the bodyside liner 44 can include a meltblown web, a spunbonded web, or a bonded-carded-web composed of natural fibers, synthetic fibers or combinations thereof. The bodyside liner 44 can be composed of a substantially hydrophobic material, and the hydrophobic material can optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 44 or can be selectively applied to particular sections of the bodyside liner 44, such as the medial section along the longitudinal center line.

The bodyside liner 44 can also be stretchable, and, more suitably, it can be elastomeric. In particular, the bodyside liner 44 is suitably stretchable and more suitably elastomeric in at least the lateral or circumferential direction 32 of the pant 10. In other aspects the bodyside liner 44 can be stretchable, and more suitably elastomeric, in both the lateral direction 32 and the longitudinal direction 30.

The absorbent structure 46 is suitably compressible, conformable, non-irritating to a wearer's skin, and capable of absorbing and retaining liquids and certain body wastes. For example, the absorbent structure 46 can include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials can be formed into a web structure by employing various conventional methods and techniques. For example, the absorbent structure 46 can be formed by a dry-forming technique, an air forming technique, a wet-forming technique, a foam-forming technique, or the like, as well as combinations thereof. Furthermore, the absorbent structure 46 can itself encompass multiple layers in a Z-direction (e.g., thickness) of the absorbent structure 46. Such multiple layers can take advantage of differences in absorbent capacity, such as by placing a lower absorbent capacity material layer closer to the bodyside liner 44 and a higher absorbent capacity material closer to the outer cover 42. Likewise, discrete portions of a single-layered absorbent structure can encompass higher capacity absorbents, and other discrete portions of the structure can encompass lower capacity absorbents.

Superabsorbent material is suitably present in the absorbent structure 46 in an amount of from about 0 to about 100 weight percent based on total weight of the absorbent structure 46. The absorbent structure 46 can suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid.

The absorbent structure 46 can alternatively include a coform material. The term "coform material" generally refers to composite materials including a mixture or stabilized matrix of thermoplastic fibers and a second non-thermoplastic material. As an example, coform materials are made by a process in which at least one meltblown die head is arranged near a chute through which other materials are added to the web while it is forming. Such other materials can include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers can be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene.

In one suitable aspect, the absorbent structure 46 is stretchable so as not to inhibit the stretchability of other components to which the absorbent structure can be adhered, such as the outer cover 42 and the bodyside liner 44. After being formed or cut to a desired shape, the absorbent structure 46 can be wrapped or encompassed by a suitable wrap (not shown) that aids in maintaining the integrity and shape of the absorbent structure 46.

The absorbent assembly 34 can also include a surge management layer (not shown) located adjacent the absorbent structure 46 (e.g., between the absorbent structure 46 and the bodyside liner 44) to help decelerate and diffuse surges or gushes of liquid that can be rapidly introduced into the absorbent structure 46 of the diaper pant 10 by the wearer. Desirably, the surge management layer can rapidly accept and temporarily hold the liquid prior to releasing the liquid into the storage or retention portions of the absorbent structure 46. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference.

The absorbent assembly 34 can also include a pair of containment flaps (not shown) that extend longitudinally along the absorbent assembly 34 and are adapted to provide a barrier to the lateral flow of body exudates as is known in the art. The containment flaps can be connected to the bodyside liner 44 or other components of the absorbent assembly 34. Suitable configurations of the containment flaps are described, for example, in U.S. Pat. No. 5,599,338 issued Feb. 4, 1997, to K. Enloe, the entirety of which is incorporated herein by reference.

Figure 3:
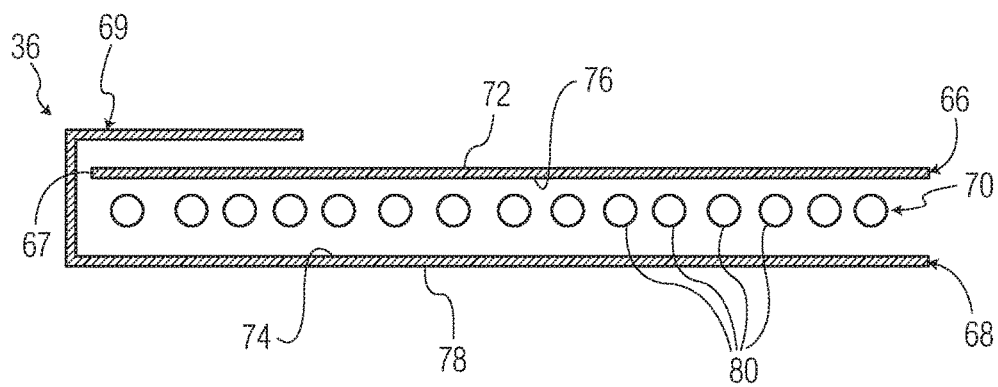
FIG. 3 a cross-section of the absorbent article of FIG. 1 taken along line "3-3" in FIG. 1.

With reference to FIG. 3, the laminate 36 used to form the front region 12 in a prior art absorbent article includes a multi-layer construction including an inner or body-facing layer 66, an outer or garment-facing layer 68, and an elastic layer 70 disposed between the body-facing layer 66 and the garment-facing layer 68. The body-facing layer 66 and the garment-facing layer 68 each include, respectively, a body-facing side 72, 74 and a garment-facing side 76, 78. The garment-facing side 76 of the body-facing layer 66 is connected to the body-facing side 74 of the garment-facing layer 68 by suitable means such as adhesives, ultrasonic bonds, thermal bonds, pressure bonds, or combinations thereof. In the illustrated aspect, an upper portion 69 of the garment-facing layer 68 is folded over a top edge 67 of the body-facing layer 66. The upper portion 69 is connected to the body-facing side 72 of the body-facing layer 66 to close the top edge 49 of the waist opening 48 (FIG. 2), and enclose the elastic layer 70 between the body-facing layer 66 and the garment-facing layer 68.

The body-facing layer 66 is constructed from a non-apertured nonwoven material. Suitable nonwovens include single layer nonwovens, such as spunbond webs, and non-woven laminates. In one suitable aspect, the body-facing layer 66 includes a spunbond/spunbond/spunbond ("SSS") laminate. In another suitable aspect, the body-facing layer 66 includes at least one meltblown layer positioned between two or more spunbond layers to form a spunbond/meltblown/spunbond ("SMS") laminate. In one particular aspect, the body-facing layer 66 includes a spunbond/spunbond/meltblown/meltblown/spunbond laminate ("SSMMS"). The nonwoven laminate can have other configurations and possess any desired number of meltblown and spunbond layers, such as spunbond/meltblown/meltblown/spunbond laminates ("SMMS"), spunbond/meltblown laminates ("SM"), etc. In addition to or as an alternative to meltblown and spunbond webs, a variety of other nonwoven webs can also be used to form the body-facing layer 66 including, for example and without limitation, through-air bonded carded webs, thermally bonded carded webs, wet-laid webs, coform webs, and hydraulically entangled webs.

The body-facing layer 66 is liquid-impermeable and vapor permeable. That is, the body-facing layer 66 permits vapors to escape from the interior of the disposable absorbent article, while still preventing liquids from passing through the body-facing layer 66. The body-facing layer 66 can be treated or otherwise processed to impart a desired level of liquid impermeability to the body-facing layer 66.

The elastic layer 70 is attached to at least one of the body-facing layer 66 and the garment-facing layer 68 to impart a desired level of elasticity to the laminate 36. The elastic layer can be attached to the body-facing layer 66 and/or the garment-facing layer 68 by any suitable means including, for example, adhesives. The elastic layer 70 can be stretched and then adhered to one or both of the body-facing layer 66 and the garment-facing layer 68, or adhered to one or both of the body-facing layer 66 and the garment-facing layer 68 when the layers 66, 68 are in a gathered state to impart a desired level of elasticity to the laminate 36. In other aspects, the elastic layer 70 is adhered to one or both of the body-facing layer 66 and the garment-facing layer 68, and then elasticized or shrunk, for example with the application of heat, such that elastic retractive forces are imparted to the laminate 36.

The elastic layer 70 can be formed of a variety of suitable elastic materials, including sheets, strands, or ribbons of natural rubber, synthetic rubber, or thermoplastic elastomeric polymers. In the illustrated aspect, the elastic layer 70 includes a plurality of elastomeric strands 80 extending in the lateral direction 32 (FIG. 1) or circumferential direction (FIG. 2) of the diaper pant 10. In one suitable aspect, the elastomeric strands 80 include dry-spun coalesced multifilament spandex elastomeric strands sold under the trade name LYCRA® and available from Invista of Wichita, Kans., U.S.A. Other suitable materials from which the elastic layer 70 can be constructed include vertical filament laminate (VFL) materials, an example of which is described in U.S. Pat. No. 6,916,750 to Thomas et al., which is hereby incorporated by reference; apertured elastic films, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are hereby incorporated by reference, and other elastic laminates such as single- and dual-faced spandex laminates, stretch-bonded laminates (SBL), and continuous filament stretch-bonded laminates (CFSBL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are hereby incorporated by reference.

The garment-facing layer 68 is vapor permeable, and can be liquid permeable or liquid impermeable. The garment-facing layer 68 can be constructed from an apertured nonwoven, such as a single layer nonwoven or a nonwoven laminate. In one suitable aspect, the garment-facing layer 68 includes a spunbond/spunbond/spunbond ("SSS") laminate. In another suitable aspect, the garment-facing layer 68 includes at least one meltblown layer positioned between two or more spunbond layers to form a spunbond/meltblown/spunbond ("SMS") laminate. In one particular aspect, the garment-facing layer 68 includes a spunbond/spunbond/meltblown/meltblown/spunbond laminate ("SSMMS"). The nonwoven laminate can have other configurations and possess any desired number of meltblown and spunbond layers, such as spunbond/meltblown/meltblown/spunbond laminates ("SMMS"), spunbond/meltblown laminates ("SM"), etc. In addition to or as an alternative to meltblown and spunbond webs, a variety of other nonwoven webs can also be used to form the body-facing layer 66 including, for example and without limitation, through-air bonded carded webs, thermally bonded carded webs, wet-laid webs, coform webs, and hydraulically entangled webs.

The body-facing layer 66 and the garment-facing layer 68 are joined together in face-to-face relationship by suitable means such as adhesives, ultrasonic bonding, thermal bonding, pressure bonding, or combinations thereof. Suitable adhesives, which can be applied continuously or intermittently as beads, a spray, parallel swirls, or the like, include elastomeric adhesives (i.e. materials capable of at least 75% elongation without rupture), such as aqueous-based styrene butadiene adhesives, neoprene, polyvinyl chloride, vinyl copolymers, polyamides, and ethylene vinyl terpolymers.

Figure 4:
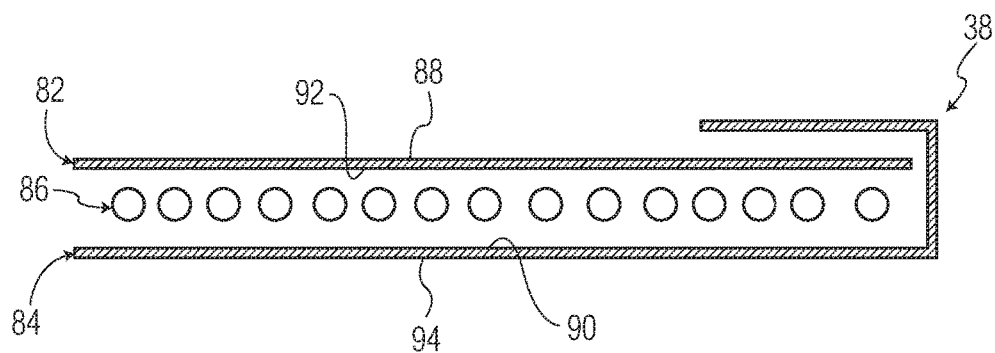
FIG. 4 is a cross-section of the absorbent article of FIG. 1 taken along line "4-4" in FIG. 1.

Referring to FIG. 4, the laminate 38 used to form the back region 14 of a prior art absorbent article has the same construction and configuration as the laminate 36 used to form the front region 12. That is, the laminate 38 includes a multi-layer construction including an inner or body-facing layer 82, an outer or garment-facing layer 84, and an elastic layer 86 disposed between the body-facing layer 82 and the garment-facing layer 84. The body-facing layer 82 and the garment-facing layer 84 each include, respectively, a body-facing side 88, 90 and a garment-facing side 92, 94. The layers 82, 84, 86 of the laminate 38 can be constructed of the same materials as the layers 66, 68, 70 of the laminate 36 described above with reference to FIG. 3.

Figure 6:
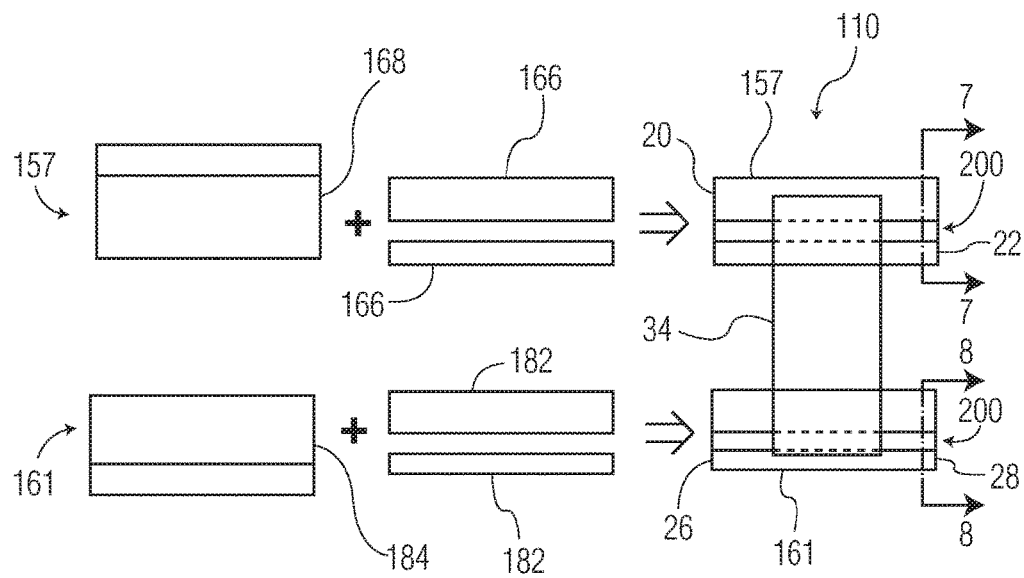
FIG. 6 is a schematic illustration of the assembly of an aspect of the absorbent article of the present disclosure with a single-layer zone in each of the front and back panels.
Figure 7:
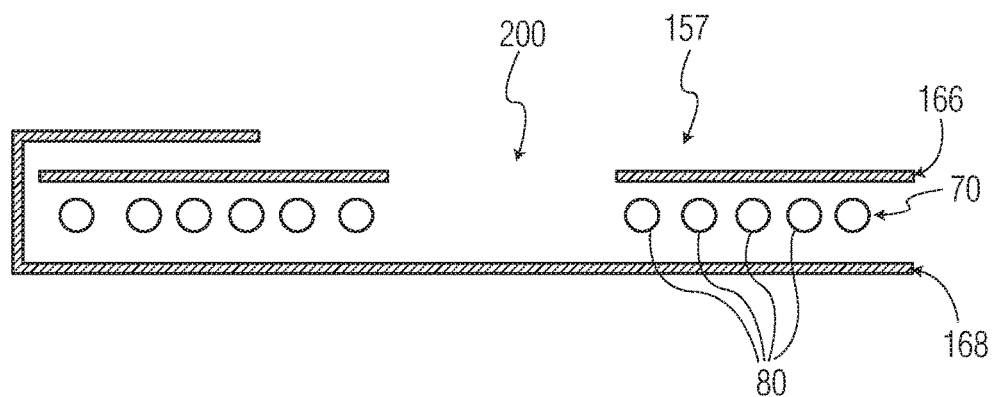
FIG. 7 is a cross-section of the absorbent article of FIG. 6 taken along line "7-7" in FIG. 6.
Figure 8:
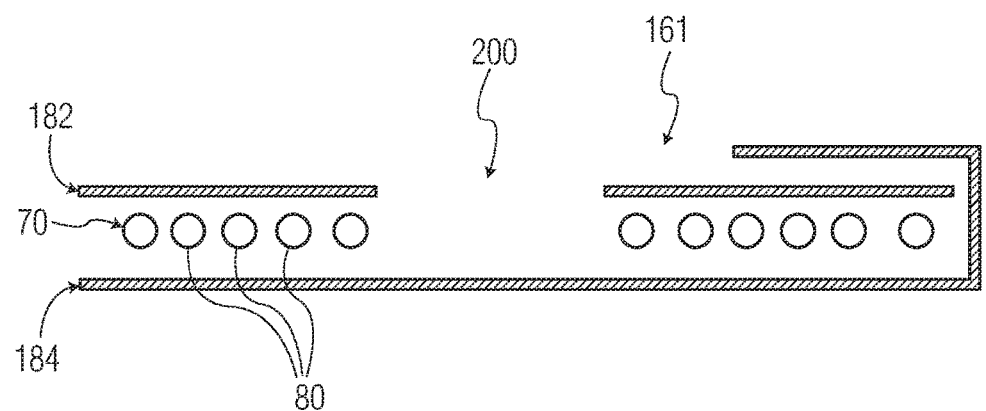
FIG. 8 is a cross-section of the absorbent article of FIG. 6 taken along line "7-7" in FIG. 6.

As illustrated in FIGS. 6-8, the absorbent article 10 can include a front panel 157 in the front region 12 and/or a back panel 161 in the back region 14. The front panel 157 includes an inner layer 166, an outer layer 168, and an elastic layer 170 that can include elastomeric strands 180 or other elastic materials. The back panel 161 includes an inner layer 182, an outer layer 184, and an elastic layer 170 that can include elastomeric strands 180 or other elastic materials. The inner layers 166, 182 are affixed to the outer layers 168, 184, respectively, with the elastic layers 170 sandwiched therebetween. These are typically affixed to each other with adhesive, although any suitable attachment means can be used. Strands 180 are typically disposed generally perpendicular to the longitudinal axis 130 and generally parallel to the lateral axis 132. The front and back panels 157, 161 provide for fit about the wearer's waist and help to seal the waist area against leakage.

In various aspects, suitable elastic materials can include, but are not limited to, sheets, strands, or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate.

In one aspect of the present disclosure, the front and/or back panels 157, 161 are constructed such that the front and/or back panels 157, 161 include a single-layer zone 200 free of inner layers 166, 182 and elastics 170. Because the single-layer zone 200 can include only outer layers 168, 184, the single-layer zone 200 can be more breathable than other areas of the front and back panels 157, 161, thus benefiting skin comfort, and also provides a visual point of distinction with respect to conventional absorbent articles.

Figure 5:
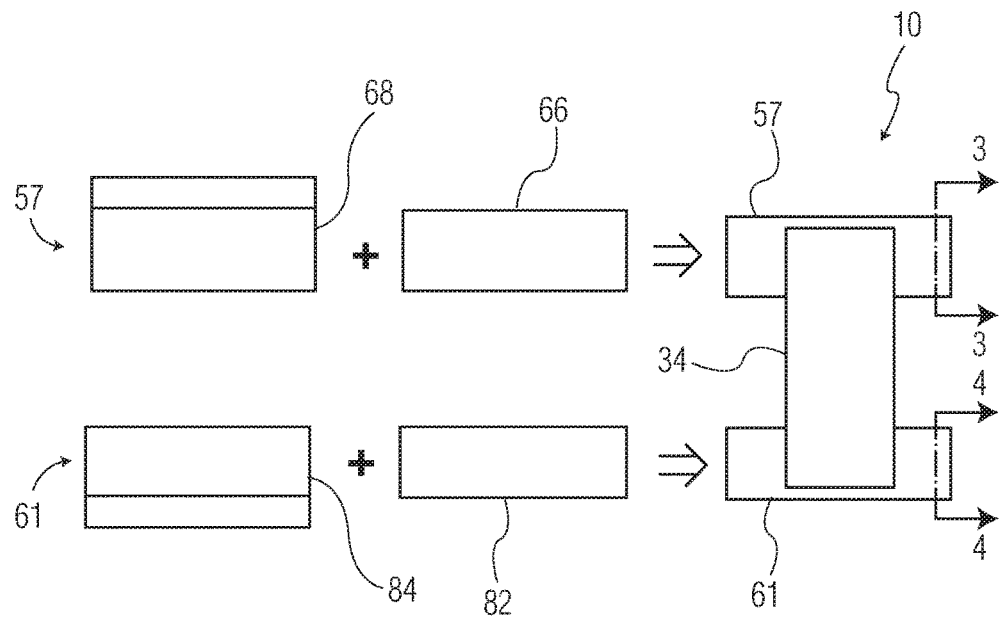
FIG. 5 is a schematic illustration of the assembly of a conventional aspect of the absorbent article of FIG. 1.

FIGS. 5-8 schematically illustrate the general arrangement of components in the absorbent articles 10, 110. FIGS. 5 and 6 are simplified to demonstrate the concept and do not include various elements of the absorbent articles 10, 110. FIG. 5 illustrates the arrangement of elements in a conventional absorbent article 10. Outer layers 68, 84 used to construct the conventional front and back panels 57, 61 are added to inner layers 66, 82 (along with elastics and adhesive, not shown) to form front and back panels 57, 61. The front and back panels 57, 61 are then affixed to a central absorbent assembly 34 to form the absorbent article 10. The central absorbent assembly 34 absorbent and covering elements described above. Cross sections of conventional panels 57, 61 are illustrated in FIGS. 3 and 4, respectively.

FIG. 6 illustrates the arrangement of elements in the absorbent article 110 of the present disclosure. In FIGS. 6-8, one or both of the front and back panels 157, 161 are substituted for the respective front and back panels 57, 61 of the absorbent article 10 of FIGS. 1-4. Outer layers 168, 184 used to construct the front and back panels 157, 161 are added to inner layers 166, 182, respectively, (along with elastics and adhesive, not shown) to form front and back panels 157, 161. In this aspect, however, the inner layers 166, 182 are added in multiple pieces with a total area less than the area of the outer layers 168, 184 such that portions of the outer layers 168, 184 are left uncovered by inner layers 166, 182. Alternatively, the inner layers 166, 182 can be added with an aperture, in segments, or in any other arrangement having a total area less than the area of outer layers 168, 184 such that portions of the outer layers 168, 184 are left uncovered by inner layers 166, 182. Further, elastic material is not added to the panels in the areas in which the outer layers 168, 184 remain uncovered. The area that is uncovered is the single-layer zone 200.

To be clear, whereas FIG. 6 illustrates both front and back panels 157, 161 including a single-layer zone 200, it is a product design decision whether one or optionally both of the front and back panels 157, 161 will be substituted for the respective front and back panels 57, 61 of the absorbent article 10 of FIGS. 1-4. If only one of the front and back panels 157, 161 is used, than the other of the front and back panels 157, 161 will not substitute for the respective front or back panel 57, 61 of the absorbent article 10 of FIGS. 1-4.

The front and/or back panels 157, 161 are then affixed to a central absorbent assembly 34 to form the absorbent article 110. The central absorbent assembly 34 includes the absorbent and covering elements described above. Cross sections of front and back panels 157, 161 of the present disclosure are illustrated in FIGS. 7 and 8. Again, only one or optionally both of the front and back panels 157, 161 illustrated in FIGS. 7 and 8 can be used. If only one of the front and back panels 157, 161 illustrated in FIGS. 7 and 8 is used, then the other of the front and back panels 157, 161 will remain as illustrated in FIG. 3 or 4.

The single-layer zone 200 can be of any suitable size or shape. In one aspect, the single-layer zone 200 extends from the first to the second front side edges 20, 22 and/or from the first to the second back side edges 26, 28, as shown in FIG. 6. The single-layer zone 200 can extend perpendicularly to the longitudinal axis 130, or in any other suitable orientation. The size, shape, position, and orientation of the single-layer zone 200 determines breathability, fit, and premium appearance.

In a first particular aspect, an absorbent article comprising includes a longitudinal axis and a lateral axis; a front region, a back region, a crotch region, the crotch region being disposed between the front region and the back region; a front panel in the front region, wherein the front panel includes an inner layer and an outer layer; a back panel in the back region, wherein the back panel includes an inner layer and an outer layer; an elastic layer disposed between the inner layer and the outer layer in the front panel; an elastic layer disposed between the inner layer and the outer layer in the back panel; and a single-layer zone in one of the front and back panels, wherein the single-layer zone is free of the inner layer and elastic layer.

A second particular aspect includes the first particular aspect, wherein the single-layer zone extends perpendicularly to the longitudinal axis.

A third particular aspect includes the first and/or second aspect, wherein each of the front and back panels includes a single-layer zone.

A fourth particular aspect includes one or more of aspects 1-3, wherein the back panel includes opposed lateral edges, and wherein the single-layer zone is in the back panel and extends from one lateral edge to the other lateral edge.

A fifth particular aspect includes one or more of aspects 1-4, wherein the front panel includes opposed lateral edges, and wherein the single-layer zone is in the front panel and extends from one lateral edge to the other lateral edge.

A sixth particular aspect includes one or more of aspects 1-5, wherein the elastic layer in the front panel is a plurality of elastic strands.

A seventh particular aspect includes one or more of aspects 1-6, wherein the elastic strands are disposed perpendicularly to the longitudinal axis.

An eighth particular aspect includes one or more of aspects 1-7, wherein the elastic layer in the back panel is a plurality of elastic strands.

A ninth particular aspect includes one or more of aspects 1-8, wherein the elastic strands are disposed perpendicularly to the longitudinal axis.

A tenth particular aspect includes one or more of aspects 1-9, further including a central absorbent assembly.

An eleventh particular aspect includes one or more of aspects 1-10, wherein the single-layer zone is in one of the front and back panels and divides the elastic layer in the one of front and back panels into two longitudinally-separate elastic layer regions.

A twelfth particular aspect includes one or more of aspects 1-11, wherein the single-layer zone is in one of the front and back panels and divides the inner layer in the one of front and back panels into two longitudinally-separate inner layer regions.

In a thirteenth particular aspect, an absorbent article includes a longitudinal axis and a lateral axis; a front region, a back region, a crotch region, the crotch region being disposed between the front region and the back region; a front panel in the front region, wherein the front panel includes an inner layer, an outer layer, and an elastic layer; a back panel in the back region, wherein the back panel includes an inner layer, an outer layer, and an elastic layer; and a single-layer zone in each of the front and back panels, wherein each single-layer zone is free of the inner layer and elastic strands.

A fourteenth particular aspect includes the fourteenth particular aspect, wherein each single-layer zone extends perpendicularly to the longitudinal axis.

A fifteenth particular aspect includes the thirteenth and/or fourteenth aspect, wherein the elastic layer in the front panel is a plurality of elastic strands.

A sixteenth particular aspect includes one or more of aspects 13-15, wherein the elastic layer in the back panel is a plurality of elastic strands.

A seventeenth particular aspect includes one or more of aspects 13-16, further including a central absorbent assembly.

An eighteenth particular aspect includes one or more of aspects 13-17, wherein the single-layer zone is in one of the front and back panels and divides the elastic layer in the one of front and back panels into two longitudinally-separate elastic layer regions.

A nineteenth particular aspect includes one or more of aspects 13-18, further including a body facing liner having a body facing surface and a garment facing surface; a backsheet coupled to the body facing liner; an absorbent body positioned between the body facing liner and the backsheet; and a first containment flap and a second containment flap, the first containment flap and the second containment flap each extending from the front end region to the back end region, the first containment flap being on a first side of the longitudinal axis, the second containment flap being on a second side of the longitudinal axis.

In a twentieth particular aspect, an absorbent article includes a longitudinal axis and a lateral axis; a front region, a back region, a crotch region, the crotch region being disposed between the front region and the back region; a central absorbent assembly; a front panel in the front region, wherein the front panel includes an inner layer, an outer layer, and a plurality of elastic strands; a back panel in the back region, wherein the back panel includes an inner layer, an outer layer, and a plurality of elastic strands; and a single-layer zone in each of the front and back panels, wherein each single-layer zone is free of the inner layer and elastic strands, and wherein each single-layer zone divides the elastic layer of the panel into two longitudinally-separate elastic layer regions In the interests of brevity and conciseness, any ranges of values set forth in this disclosure contemplate all values within the range and are to be construed as support for claims reciting any sub-ranges having endpoints that are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by references, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. An absorbent article comprising:
a longitudinal axis and a lateral axis;
a front region, a back region, a crotch region, the crotch region being disposed between the front region and the back region;
a front panel in the front region, wherein the front panel includes an inner layer and an outer layer;
a back panel in the back region, wherein the back panel includes an inner layer and an outer layer;
an elastic layer disposed between the inner layer and the outer layer in the front panel;
an elastic layer disposed between the inner layer and the outer layer in the back panel; and
a single-layer zone in one of the front and back panels, wherein the single-layer zone is free of the inner layer and elastic layer.

2. The article of claim 1, wherein the single-layer zone extends perpendicularly to the longitudinal axis.

3. The article of claim 1, wherein each of the front and back panels includes a single-layer zone.

4. The article of claim 1, wherein the back panel includes opposed lateral edges, and wherein the single-layer zone is in the back panel and extends from one lateral edge to the other lateral edge.

5. The article of claim 1, wherein the front panel includes opposed lateral edges, and wherein the single-layer zone is in the front panel and extends from one lateral edge to the other lateral edge.

6. The article of claim 1, wherein the elastic layer in the front panel is a plurality of elastic strands.

7. The article of claim 6, wherein the elastic strands are disposed perpendicularly to the longitudinal axis.

8. The article of claim 1, wherein the elastic layer in the back panel is a plurality of elastic strands.

9. The article of claim 8, wherein the elastic strands are disposed perpendicularly to the longitudinal axis.

10. The article of claim 1, further comprising a central absorbent assembly.

11. The article of claim 1, wherein the single-layer zone is in one of the front and back panels and divides the elastic layer in the one of front and back panels into two longitudinally-separate elastic layer regions.

12. The article of claim 1, wherein the single-layer zone is in one of the front and back panels and divides the inner layer in the one of front and back panels into two longitudinally-separate inner layer regions.

13. An absorbent article comprising:
a longitudinal axis and a lateral axis;
a front region, a back region, a crotch region, the crotch region being disposed between the front region and the back region;
a front panel in the front region, wherein the front panel includes an inner layer, an outer layer, and an elastic layer;
a back panel in the back region, wherein the back panel includes an inner layer, an outer layer, and an elastic layer; and
a single-layer zone in each of the front and back panels, wherein each single-layer zone is free of the inner layer and elastic strands.

14. The article of claim 13, wherein each single-layer zone extends perpendicularly to the longitudinal axis.

15. The article of claim 13, wherein the elastic layer in the front panel is a plurality of elastic strands.

16. The article of claim 13, wherein the elastic layer in the back panel is a plurality of elastic strands.

17. The article of claim 13, further comprising a central absorbent assembly.

18. The article of claim 13, wherein the single-layer zone is in one of the front and back panels and divides the elastic layer in the one of front and back panels into two longitudinally-separate elastic layer regions.

19. The article of claim 13, further comprising:
a body facing liner having a body facing surface and a garment facing surface;
a backsheet coupled to the body facing liner;
an absorbent body positioned between the body facing liner and the backsheet; and
a first containment flap and a second containment flap, the first containment flap and the second containment flap each extending from the front end region to the back end region, the first containment flap being on a first side of the longitudinal axis, the second containment flap being on a second side of the longitudinal axis.

20. An absorbent article comprising:
a longitudinal axis and a lateral axis;
a front region, a back region, a crotch region, the crotch region being disposed between the front region and the back region;
a central absorbent assembly;
a front panel in the front region, wherein the front panel includes an inner layer, an outer layer, and a plurality of elastic strands;
a back panel in the back region, wherein the back panel includes an inner layer, an outer layer, and a plurality of elastic strands; and
a single-layer zone in each of the front and back panels, wherein each single-layer zone is free of the inner layer and elastic strands, and wherein each single-layer zone divides the elastic layer of the panel into two longitudinally-separate elastic layer regions.

* * * * *